US010525215B2

(12) United States Patent
Davidson

(10) Patent No.: US 10,525,215 B2
(45) Date of Patent: Jan. 7, 2020

(54) SYSTEM FOR EFFICIENTLY GENERATING AND INHALING VAPORS OF HERBS AND INCENSE

(71) Applicant: Wesley Davidson, Boynton Beach, FL (US)

(72) Inventor: Wesley Davidson, Boynton Beach, FL (US)

(*) Notice: Subject to any disclaimer, the term of this patent is extended or adjusted under 35 U.S.C. 154(b) by 1093 days.

(21) Appl. No.: 14/937,428

(22) Filed: Nov. 10, 2015

(65) Prior Publication Data

US 2017/0128682 A1    May 11, 2017

(51) Int. Cl.
*A61M 15/00*    (2006.01)
*A61M 15/06*    (2006.01)
*A24F 1/30*    (2006.01)
*A61M 11/04*    (2006.01)

(52) U.S. Cl.
CPC .......... *A61M 15/0086* (2013.01); *A24F 1/30* (2013.01); *A61M 11/048* (2014.02); *A61M 15/002* (2014.02); *A61M 15/06* (2013.01); *A61M 2205/0211* (2013.01); *A61M 2205/7545* (2013.01)

(58) Field of Classification Search
CPC .......... F24F 1/16; F24F 1/30; A61M 11/048; A61M 11/042; A61M 15/0086; A61M 15/042; A61M 15/06; A61M 2205/7545; A61M 16/105; A61M 16/1095
USPC ....................................................... 131/173
See application file for complete search history.

(56) References Cited

U.S. PATENT DOCUMENTS

| 223,058 | A | | 5/1879 | Morrison | |
|---|---|---|---|---|---|
| 3,703,179 | A | * | 11/1972 | Nubla | A24F 1/30 131/173 |
| 4,244,383 | A | * | 1/1981 | Kahler | A24F 5/00 131/173 |
| 6,488,028 | B1 | * | 12/2002 | Lambert | A61M 16/009 128/204.13 |
| 6,761,164 | B2 | | 7/2004 | Amirpour et al. | |
| 7,475,684 | B2 | | 1/2009 | Balch et al. | |
| 8,479,746 | B1 | * | 7/2013 | Tannous | A24F 1/30 131/243 |
| 2002/0069886 | A1 | * | 6/2002 | Couch | A24F 1/30 131/173 |
| 2009/0078253 | A1 | | 3/2009 | Bao | |

(Continued)

*Primary Examiner* — Colin W Stuart
*Assistant Examiner* — Douglas Y Sul
(74) *Attorney, Agent, or Firm* — Melvin K. Silverman

(57) ABSTRACT

A system for generating and inhaling vapor of herbs includes a container, a base, a mouth, and an upper surface. An aperture in the surface displaced from a lip of the mouth. The container shown partially filled with water, and a diffuser positioned upon the water. The region within the container above the diffuser defines a vapor chamber. A diagonally-oriented tube includes upper and lower end secured within the aperture. Herbs are placed in an upper end of an herb-burning bowl and a lower end of the bowl having a filter limiting debris from entering the water. An inhalation cylinder having upper end attachable within an open mouth. A vacuum pump includes vacuum input from cylinder and positive pressure output about a level of the vacuum input. The pump providing pressure from bottom to top of the inhalation cylinder and the water surface diffuser to the mouth.

10 Claims, 3 Drawing Sheets

(56) References Cited

U.S. PATENT DOCUMENTS

| | | | |
|---|---|---|---|
| 2010/0126517 A1* | 5/2010 | Groff | A24F 1/30 131/173 |
| 2010/0319716 A1* | 12/2010 | Tao | A24F 1/30 131/173 |
| 2011/0079231 A1* | 4/2011 | Borushek | A24F 1/30 131/229 |
| 2012/0255566 A1* | 10/2012 | Shakouri Moghadam | A24F 1/30 131/173 |
| 2013/0104738 A1* | 5/2013 | Goldstein | B01D 53/14 95/214 |
| 2014/0246025 A1* | 9/2014 | Cragg | A61M 16/208 128/204.19 |
| 2015/0122276 A1* | 5/2015 | Johnson | A24D 3/04 131/329 |
| 2016/0324212 A1* | 11/2016 | Cameron | A24F 47/008 |
| 2017/0013882 A1* | 1/2017 | Liu | A24F 47/008 |
| 2017/0106153 A1* | 4/2017 | Davidson | A61K 9/007 |

\* cited by examiner

US 10,525,215 B2

SYSTEM FOR EFFICIENTLY GENERATING AND INHALING VAPORS OF HERBS AND INCENSE

BACKGROUND OF THE INVENTION

1. Field of the Invention

This invention relates generally to inhalation devices, and more specifically, to devices for extracting ingredients from a natural substance through vaporization.

2. Description of Prior Art

Herbs and vapors have been employed for medicinal purposes for essentially as long as human history. Even in ancient times, particular articles were employed to maximize the extraction and effective inhalation of various herbs, incense and the like. For example, such devices first appeared in U.S. patents in 1879 as U.S. Pat. No. 223,058 to Morrison. The prior art is, more recently, reflected in U.S. Pat. No. 6,761,164 (2004) to Amirpour; U.S. Publication No. 2009/0078253 to Bao; and U.S. Pat. No. 7,475,684 (2009) to Balch et al.

None of the above art however is completely adequate or cost-effective for the use of many herbs and the like which are used today. The present invention seeks to fulfill this long-felt need in the art.

SUMMARY OF THE INVENTION

The system of the invention relates to efficiently generating and inhaling vapor of herbs and incense. The system more particularly includes a hollow container having a stable base and an open mouth in an upper surface of said container, said container having an aperture in said upper surface, said aperture displaced from a lip of said open mouth, said container partially filled with water. Further included diffuser positioned substantially upon a surface of said water within said container, a region within said container above said diffuser defining a vapor collection chamber. The invention also employ a diagonally-oriented tube having an upper and a lower end, said tube secured between said aperture and said diffuser, said upper end defining an herb-burning bowl within which are placed herbs to be burned, said lower end comprising a filter, said end immersed in said water, said filter permitting vapor to escape therefrom into said water but limiting escape into said water of herbal debris of said herb-burning bowl of said tube. Also provided is an inhalation cylinder having an upper end and a lower end, said lower end selectably attachable within a periphery of said open mouth of said container and in fluid communication therewith. Further, and included is a vacuum pump located proximally and externally of said inhalation cylinder providing a vacuum input from a bottom of said cylinder and a fluid output into said cylinder above a level of said vacuum input, said vacuum pump producing a gaseous pressure gradient from bottom to top of said inhalation cylinder and from said water surface diffuser to said mouth of said container.

It is accordingly an object of the present invention to provide an effective system for the use, generation and inhalation of vapors of various herbs and incense.

It is another object to provide a system of the above type having enhanced value for medicinal purposes.

It is a further object to provide an invention of the above type which is more efficient and effective in deriving usable vapor from a given quantity of herbs and incense.

It is a yet further object to provide a system in which vapors of herbs and incense may be provided to the user while minimizing harshness otherwise associated with debris and other artifacts of the burning thereof.

The above and yet other objects and advantages of the present invention will become apparent from the hereinafter set forth Brief Description of the Drawings, Detailed Description of the Invention, and Claims appended herewith.

DETAILED DESCRIPTION OF THE INVENTION

Figure 1:
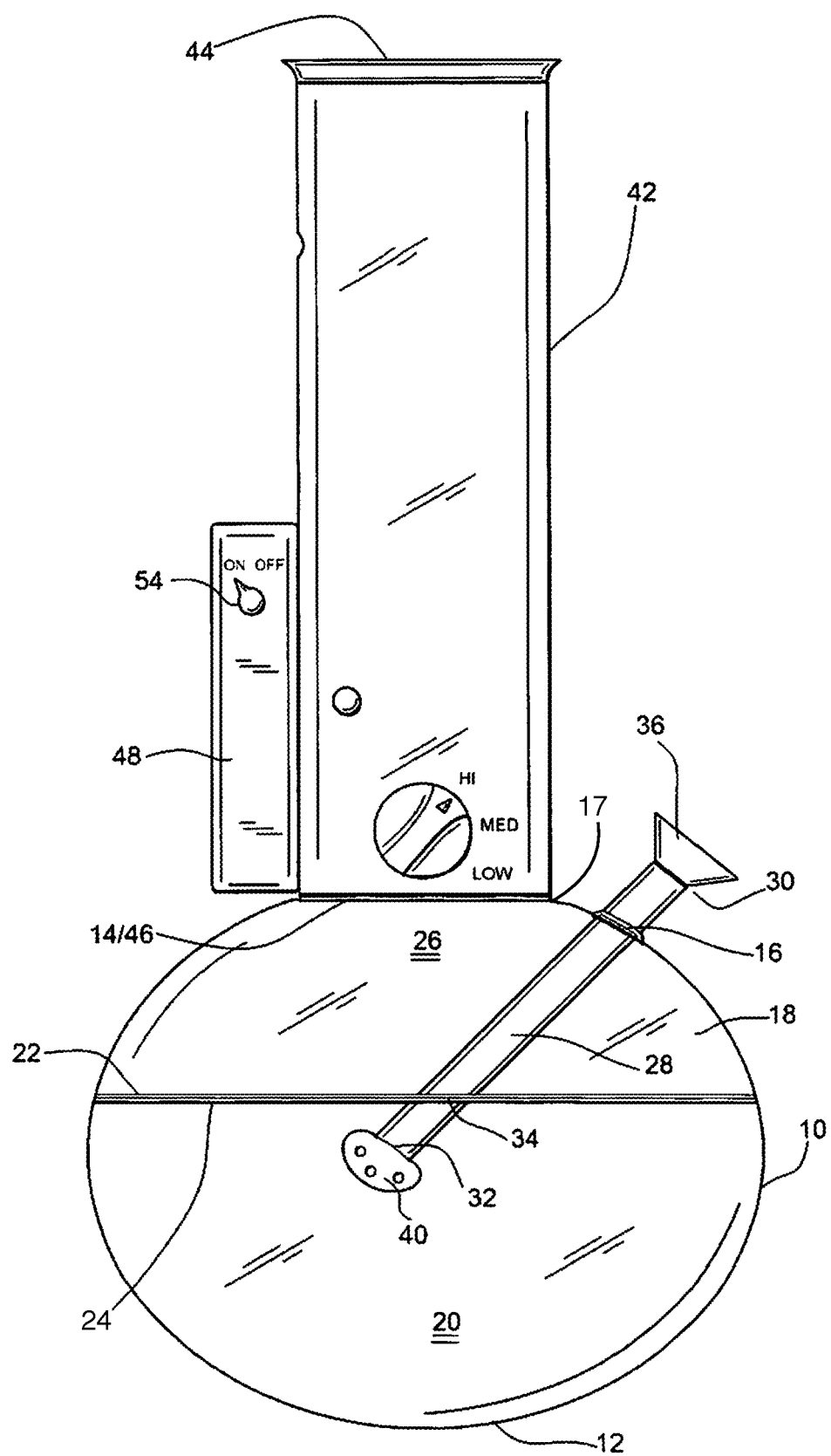
FIG. 1 is a front elevational view of the inventive system.

With reference to FIG. 1, the basic elements of the present invention may be seen to include a hollow preferably spherical container 10 having a stable base 12 and a mouth 14 at an uppermost pole of the container. Said container 10 includes an aperture 16 and an upper region 18. As may be noted, the aperture 16 is displaced from a lip 17 of said mouth 14 preferably at an angle of about 45 degrees from said pole of the spherical container. In operation, container 10 is filled with water 20 up to about level 22, at which is placed a circular diffusion element 24 which is positioned substantially upon the surface of water 20. Diffuser 24 also defines a vapor collection chamber 26 within approximately the upper hemisphere of container 10. Resultant thereof, container 10 is essentially separated into a water container generally in its lower hemisphere and a vapor collection chamber 26 generally in its upper hemisphere, the purpose thereof being to permit vapor without debris to pass through diffuser 24 while debris associated with the burning of incense or herbs (described below) falls into water 20.

The system shown in FIG. 1 further includes a diagonally oriented tube having an upper end 30 and a lower end 32 in which said tube 28 is secured within aperture 16 which may include a sleeve for purposes of stability. Such securement is also facilitated by the positioning of lower end 32 of tube 28 within an aperture 34 located within and near the center of diffusion element 24. In other words, the coaction of apertures 16 and 34 define an angulation of tube 28 relative to the base of spherical container 10.

At said upper end 30 of diagonal tube 28 is provided an herb or incense burning bowl 36 within which are placed herbs 38 which are to be burned. (See FIG. 2). Said bowl may comprise a ceramic within which thermal resistance elements may be provided for heating purposes.

Provided at lower end 32 of tube 28 is a filter 40 which, together with said end 32, are immersed in water 20. Thereby, vapor is permitted to escape from filter 40 into said water and through said diffusion element 24 therein reaching vapor region 26 of the spherical container. This arrangement limits escape of most of the burnt herbs to water 20, facilitating that of vapor into region 26, but also facilitates the acquisition of solid debris of the burning process within the water containing lower region of the spherical container.

Above container 10 is shown an elongate inhalation cylinder 42 having, for example, a diameter of 4 centimeters. Said inhalation cylinder exhibits an upper end 44 and a lower end 46 in which said lower end 46 is attachable within a periphery of open mouth 14 of container 10 as by threading means by which fluid communication therebetween is maintained. Between uses cylinder 42 is unscrewed and the water therein is emptied.

Figure 2:
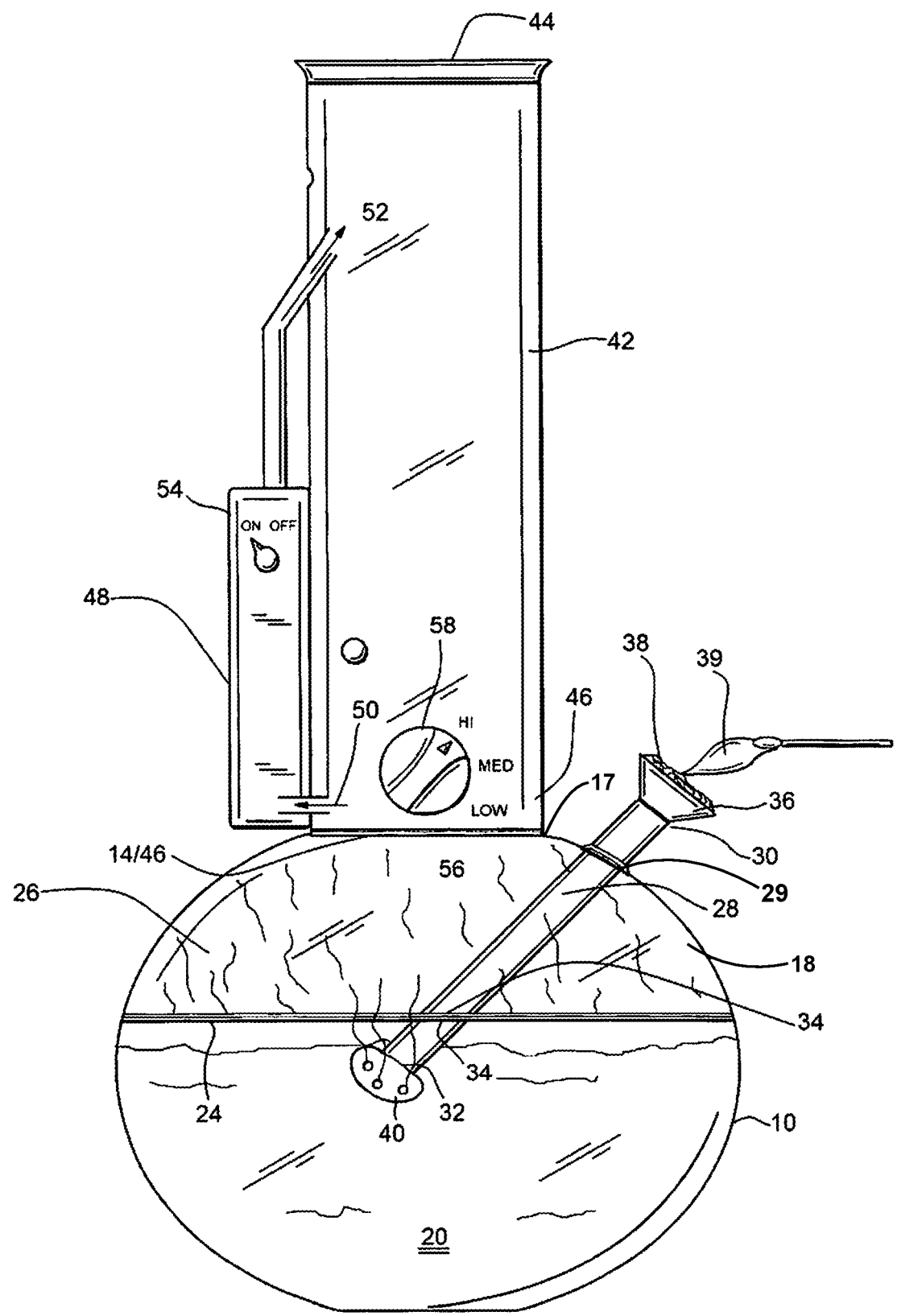
FIG. 2 is a front elevational view similar to that of FIG. 1, however showing the addition thereof of an interface between a vacuum pump and the inhalation tube of the system and also showing a part of the base thereof filled with water.

In FIG. 2, shown to the left of inhalation tube 44 is a vacuum pump 48 which is located externally of the inhalation cylinder and preferably in contact therewith. The vacuum pump includes a vacuum input 50 and a positive fluid pressure output 52, the result of which is to facilitate upward movement of vapor from the lower portion to the upper portion of inhalation cylinder 42. As such, a pressure gradient from bottom to top of cylinder is maintained including between the level of diffusion element 24 and the top 44 of the inhalation cylinder 42. As may be noted, an on-off control 54 is provided for vacuum pump 48 which is provided with an internal filter (not shown).

Figure 3:
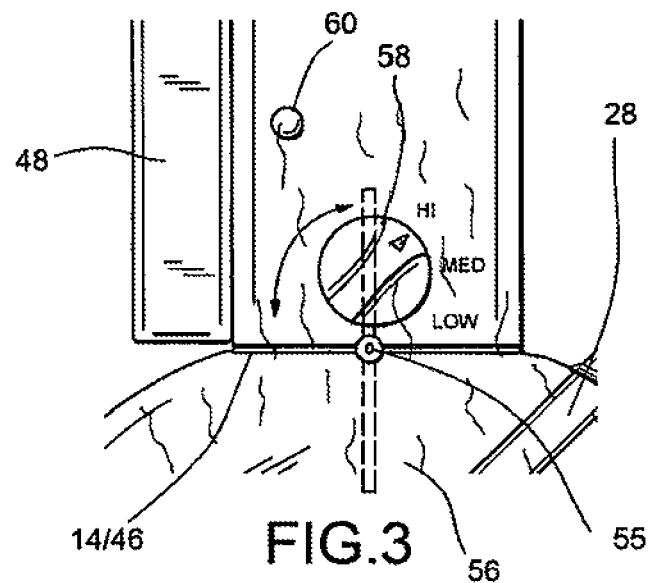
FIG. 3 is an enlarged view of the interface between the inhalation tube and the hollow spherical base of the system.
Figure 4:
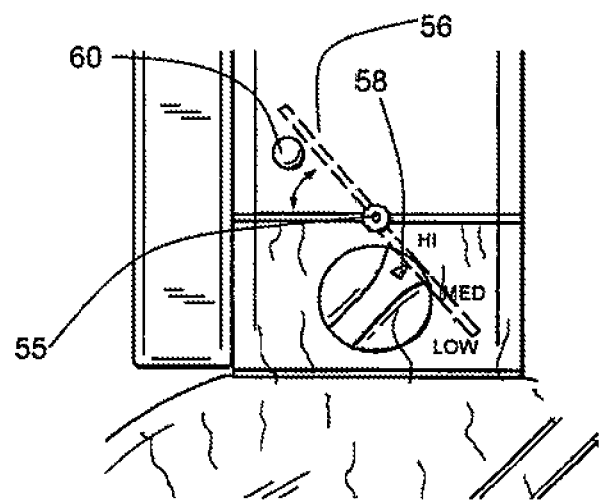
FIG. 4 is a view, similar to that of FIG. 3, however showing a 90 degree rotation of a filtration surface controlling the extent of gaseous communication between the vapor collection region and the bottom of the inhalation tube.

The extent of gaseous communication between upper region 26 of container 10 and lower region 46 of the inhalation cylinder is controlled by a gaseous communication controller through the use or a rotatable filter 56 (see FIGS. 3-4) which is axially secured upon a diameter of interface 14/46 between spherical container 10 and lower portion 46 of the inhalation cylinder 42. As may be seen in FIGS. 2-4 filter 56 may be rotated upon said axis 55 by the action of a cam element 58 in which the extent of rotation of filter 56 is defined by stop 60 (see FIG. 4). As may be appreciated, the assembly for selectably controlling the extent of communication between vapor collection chamber 26 and bottom 46 of the inhalation cylinder may be varied in a complete closure of filter 56 as is shown in FIG. 2, to that of an essentially open closure of the 14/46 interface through the condition of FIG. 3. FIG. 4 shows a partial closure of filter 56 relative to the 14/46 interface and that element 58 may be positioned beneath filter 56. Thereby, using element 58, the present system is able to control the quantity of vapor passing from upper container region 36 to inhalation cylinder 44 while controlling the rate of movement of vapor from bottom to top of the inhalation cylinder 42 through the use of vacuum pump 48. Element 54 is an on-off control for pump 48.

It is noted that a heater may be provided within ceramic bowl 36 in lieu of the use of a match or lighter 39. Where such a heater is employed, a battery is required to power the heater. Further, a motor powered spiral fan 29 may be provided internally within diagonal tube 28 to accelerate movement of vapor from to the upper end 30 of the diagonal tube to filter 40 at the bottom thereof. In one embodiment, the entirety of tube 28 may be formed of a ceramic material.

In a preferred embodiment, spherical container 10 and inhalation cylinder tube 42 formed of glass in which a preferred equatorial diameter of container 10 is in a range of 12 to 13 centimeters. A preferred length of diagonal tube 28 is about 8 centimeters.

The within system is sold under the commercial name VAC BONG.

While there has been shown and described above the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

I claim:

1. A system for efficiently generating and inhaling vapor of herbs and incense, the system comprising:
   (a) a hollow container having a stable base and an open mouth in an upper surface of said container, said container having an aperture in said upper surface, said aperture displaced from a lip of said open mouth, but above said container partially about a mid-line filled with water;
   (b) a diffuser positioned upon a surface of said water within said container, a region within said container above said diffuser defining a vapor collection chamber;
   (c) a diagonally-oriented tube having an upper and a lower end, said tube secured at one end within said aperture and at an opposite end within said diffuser, said upper end defining a bowl for receipt of herbs to be burned, said opposite end comprising a filter, said lower end immersed in said water, said filter permitting vapor to escape therefrom into said water, limiting escape into said water of herbal debris of said herb-burning bowl of said tube smaller than the filtration size of said filter;
   (d) an inhalation cylinder having an upper end and a lower end, said lower end selectably attachable within a periphery of said open mouth of said container and in fluid communication therewith;
   (e) a vacuum pump located proximally and externally of said inhalation cylinder having a vacuum input from said cylinder and a fluid pressure output into said cylinder above a level of said vacuum input, said vacuum pump producing a gaseous pressure gradient from bottom to top of said inhalation cylinder and from said diffuser to said mouth of said container;
   (f) said a gaseous communication controller including a cam and a rotatable filter, said rotatable filter having a smaller diameter than that of said mouth of said inhalation cylinder is provided therein;
   (g) said gaseous communication controller between said vapor collection chamber and said bottom of the inhalation cylinder, said gaseous communication controller selectably controllable; and
   (h) said cam controlling a degree of rotation of said rotatable filter about a diametric axis of said aperture.

2. The system as recited in claim 1, further comprising:
   (i) a heater within said bowl of said diagonal tube.

3. The system as recited in claim 1, said vacuum pump filtering herbal debris from herbal smoke if a mixture thereof passes through said rotatable filter, only permitting herbal smoke to pass upwardly in said inhalation cylinder.

4. The system as recited in claim 3, in which said motor cam of said gaseous communication controller includes settings of high, low, medium and off.

5. The system as recited in claim 1, in which said rotation control cam of said rotatable filter actuates a selectable degree of rotation of said rotatable filter about a diametric axis of said aperture.

6. The system as recited in claim 5, in which said both container and said cylinder comprise glass.

7. The system as recited in claim 6, in which said container defines a spherical shape.

8. The system as recited in claim 1, in which said bowl comprises a ceramic.

9. The system as recited in claim 1, in which said diagonal tube comprises a ceramic material having heating element in said bowl.

10. The system as recited in claim 9, including a spiral fan with said diagonal tube.

* * * * *